United States Patent
Cordaro et al.

(10) Patent No.: US 9,437,331 B2
(45) Date of Patent: Sep. 6, 2016

(54) INHERENTLY SAFE PASSIVE GAS MONITORING SYSTEM

(71) Applicant: Savannah River Nuclear Solutions, LLC, Aiken, SC (US)

(72) Inventors: Joseph V. Cordaro, Martinez, GA (US); John Stephen Bellamy, Aiken, SC (US); James M. Shuler, Germantown, MD (US); Davis J. Shull, Batesburg, SC (US); Daniel R. Leduc, Edgefield, SC (US)

(73) Assignee: Savannah River Nuclear Solutions, LLC, Aiken, SC (US)

( * ) Notice: Subject to any disclaimer, the term of this patent is extended or adjusted under 35 U.S.C. 154(b) by 261 days.

(21) Appl. No.: 14/182,608

(22) Filed: Feb. 18, 2014

(65) Prior Publication Data
US 2015/0233882 A1 Aug. 20, 2015

(51) Int. Cl.
*H04B 5/02* (2006.01)
*G21C 17/06* (2006.01)
*G01N 33/00* (2006.01)
*H04B 5/00* (2006.01)

(52) U.S. Cl.
CPC ........... *G21C 17/06* (2013.01); *G01N 33/0036* (2013.01); *H02J 50/10* (2016.02); *H04B 5/0037* (2013.01)

(58) Field of Classification Search
CPC . H02J 5/005; G01N 33/0036; H04B 5/0037; G21C 17/06
See application file for complete search history.

(56) References Cited

U.S. PATENT DOCUMENTS

| | | | |
|---|---|---|---|
| 5,012,672 A | 5/1991 | Mckee | |
| 5,282,229 A | 1/1994 | Ukai et al. | |
| 5,610,340 A * | 3/1997 | Carr | G01L 9/0073 73/718 |
| 6,111,409 A | 8/2000 | Edwards et al. | |
| 6,252,923 B1 | 6/2001 | Iacovino et al. | |
| 6,486,666 B1 | 11/2002 | Grossmann et al. | |
| 6,583,618 B2 | 6/2003 | McClelland | |
| 6,888,434 B2 | 5/2005 | Nordberg | |

(Continued)

FOREIGN PATENT DOCUMENTS

| | | |
|---|---|---|
| CN | 101493371 | 7/2009 |
| WO | WO 2006/104373 | 10/2006 |

(Continued)

OTHER PUBLICATIONS

Raghunathan, Vijay, et al. "Energy-aware wireless microsensor networks."Signal Processing Magazine, IEEE 19.2 (2002): 40-50.*

(Continued)

*Primary Examiner* — Lisa Caputo
*Assistant Examiner* — Punam Roy
(74) *Attorney, Agent, or Firm* — Dority & Manning, P.A.

(57) ABSTRACT

Generally, the present disclosure is directed to gas monitoring systems that use inductive power transfer to safely power an electrically passive device included within a nuclear material storage container. In particular, the electrically passive device can include an inductive power receiver for receiving inductive power transfer through a wall of the nuclear material storage container. The power received by the inductive power receiver can be used to power one or more sensors included in the device. Thus, the device is not required to include active power generation components such as, for example, a battery, that increase the risk of a spark igniting flammable gases within the container.

19 Claims, 7 Drawing Sheets

(56) References Cited

U.S. PATENT DOCUMENTS

| | | | |
|---|---|---|---|
| 7,142,625 | B2 | 11/2006 | Jones et al. |
| 7,619,523 | B2* | 11/2009 | Durtschi ............ G06Q 10/087 340/572.1 |
| 8,400,017 | B2 | 3/2013 | Kurs et al. |
| 8,482,250 | B2 | 7/2013 | Soar |
| 8,594,572 | B1* | 11/2013 | Ortiz ................... H02J 5/005 307/104 |
| 8,636,883 | B2* | 1/2014 | Hoagland ........... G01N 27/122 204/400 |
| 2002/0046957 | A1 | 4/2002 | Hough et al. |
| 2004/0193379 | A1 | 9/2004 | Lillis et al. |
| 2005/0272167 | A1 | 12/2005 | Andino |
| 2006/0255943 | A1 | 11/2006 | Hougen et al. |
| 2007/0209937 | A1* | 9/2007 | Hoagland ........... G01N 27/122 204/424 |
| 2008/0245422 | A1 | 10/2008 | McTargett |
| 2011/0200153 | A1 | 8/2011 | Ferreira, Jr. |
| 2013/0034198 | A1 | 2/2013 | Chandrasekharan |
| 2013/0249479 | A1 | 9/2013 | Partovi |
| 2015/0256015 | A1* | 9/2015 | Gudan ................. H02J 7/345 307/104 |

FOREIGN PATENT DOCUMENTS

| | | | |
|---|---|---|---|
| WO | WO 2007128857 A1 * | 11/2007 | ......... A61N 1/37223 |
| WO | WO 2013/128355 | 9/2013 | |

OTHER PUBLICATIONS

Constantinou, P., et al. "An energy supply unit for an autonomous remote sensor system monitoring stored nuclear waste." Sensors and Actuators A: Physical 166.1 (2011): 52-65.*

Carstens, Thomas, et al. "Thermoelectric powered wireless sensors for spent fuel monitoring." Nuclear Science, IEEE Transactions on 59.4 (2012): 1408-1413.*

Carstens, Thomas A., et al. "Thermoelectric Powered Wireless Sensors for Dry-Cask Storage." Nuclear Science, IEEE Transactions on 60.2 (2013): 1072-1079.*

Jia, Yi, et al. "Design and characterization of a passive wireless strain sensor." Measurement Science and Technology 17.11 (2006): 2869.*

Kaiser, Todd J. "Passive telemetric readout system." Sensors Journal, IEEE6.5 (2006): 1340-1345.*

Ong, Keat Ghee, Kefeng Zeng, and Craig A. Grimes. "A wireless, passive carbon nanotube-based gas sensor." sensors Journal, IEEE 2.2 (2002): 82-88.*

Ong, Keat Ghee, et al. "Design and application of a wireless, passive, resonant-circuit environmental monitoring sensor." Sensors and Actuators A: Physical 93.1 (2001): 33-43.*

Lenz, James E. "A Review of Magnetic Sensors". Proceedings of the IEEE, vol. 78, No. 6, Jun. 1990, pp. 973-989.

Aleixandre et al. "Development of fiber optic hydrogen sensors for testing nuclear waste repositories". Sensors and Actuators B: Chemical, vol. 107, Issue 1, May 27, 2005, pp. 113-120.

Jones et al. "Detection of shielded nuclear material in a cargo container". Nuclear Instruments and Methods in Physics Research Section A: Accelerators, Spectrometers, Detectors and Associated Equipment, vol. 562, Issue 2, Jun. 23, 2006, pp. 1085-1088.

Pruitt et al. "Piezoresistive cantilevers and measurement system for characterizing low force electrical contacts". Sensors and Actuators A: Physical, vol. 104, Issue 1, Mar. 15, 2003, pp. 68-77.

L-STM-A-00003 Revision 0-9977 Type B Packaging Internal Data Collection Feasibility Testing—Magnetic Field Communications. Savannah River National Laboratory. May 2012, 16 pages.

"EC410 Electrochemcial Sensor Oxygen." *SGX Sensortech*, e2v technologies, Oct. 2009, Web. Dec. 20, 2013, 2 pages.

"KHS-200 MEMS Micro-Pellistor Hydrogen Sensor. " Kebaili. com, Kebaili Corporation, Web. Dec. 20, 2013, 2 pages.

Chen et al. "ARG-US-An RFID-Based Tracking and Monitoring System for Nuclear Material Packages" Decision and Information Sciences, Argonne National Laboratory, Aug. 2013, 8 pages.

PCT International search Report for corresponding PCT Application No. PCT/US2015/016010, mailed on May 20, 2015, 2 pages.

* cited by examiner $$V_{OUT} = V_{IN}\left[\frac{R_3}{R_3+R_g} = \frac{R_2}{R_1+R_2}\right]$$

INHERENTLY SAFE PASSIVE GAS MONITORING SYSTEM

FEDERAL RESEARCH STATEMENT

This invention was made with Government support under Contract No. DE-AC09-085R22470, awarded by the U.S. Department of Energy. The Government has certain rights in the invention.

FIELD OF THE INVENTION

The present disclosure relates generally to gas monitoring systems for inclusion within a nuclear material storage container. More particularly, the present disclosure is directed to gas monitoring systems that use inductive power transfer to safely power one or more passive sensors included within a nuclear material storage container.

BACKGROUND OF THE INVENTION

Containers and associated systems used to store and ship radioactive materials such as nuclear waste must be designed and demonstrated to safely contain the radioactive materials and limit personnel exposure both under normal conditions and in a variety of accident scenarios.

As an example, one of the greater challenges in the recovery of Plutonium Oxide located in the United States and around the world is dealing with the potential generation of hydrogen and oxygen theoretically forming a flammable gas in the vapor spaces of a container storing the material.

Thus, a container that includes one or more sensors, such as, for example, sensors for measuring hydrogen concentration, oxygen concentration, pressure within the container, and/or temperature within the container would be valuable, as it would allow confirmation of safe conditions prior to shipment of the container or periodically during storage of container.

However, due to the flammable nature of the hydrogen and oxygen gases potentially forming within the vapor spaces of the container, inclusion and powering of such sensors increases the risk of accidental combustion. In particular, inclusion of a battery within the container to power the sensors introduces the possibility of a spark event at the battery, which could potentially ignite any flammable vapors present.

In addition, certain radioactive materials may require storage for a significant length of time. However, typical batteries have a limited lifespan. As such, a storage container that includes a battery to power one or more internal sensors may be unable to provide readings or otherwise properly perform over the entirety of an extended storage period.

BRIEF DESCRIPTION OF THE INVENTION

Additional aspects and advantages of the invention will be set forth in part in the following description, or may be apparent from the description, or may be learned through practice of the invention.

One aspect of the present disclosure is directed to a passive gas monitoring system. The system includes an inductive power receiver positioned within a nuclear material storage container. The inductive power receiver is configured to receive power from an inductive power transmitter positioned outside the nuclear material storage container using inductive power transfer. The system includes one or more sensors positioned within the nuclear material storage container. The one or more sensors are configured to respectively provide one or more outputs respectively describing one or more conditions within the nuclear material storage container. The one or more sensors receive power from the inductive power receiver. The system includes at least one data transmitter positioned within the nuclear material storage container. The at least one data transmitter is configured to transmit the one or more outputs respectively provided by the one or more sensors to a data receiver positioned outside the nuclear material storage container.

Another aspect of the present disclosure is directed to a device for measuring gas characteristics within a radioactive material container. The device includes an inductive power receiver for receiving inductive power transfer through a wall of the radioactive material container. The device includes a rectifier coupled to the inductive power receiver. The device includes at least one of an oxygen concentration sensor or a hydrogen concentration sensor coupled to an output of the rectifier. The device includes at least one data transmission component for receiving data from the at least one of the oxygen concentration sensor and the hydrogen concentration sensor and transmitting the data to a data receiver that is external to the radioactive material container. The device does not contain any power generation components such that the device is wholly passive in nature.

Another aspect of the present disclosure is directed to an electrically passive device for providing data describing one or more conditions existing within a nuclear material storage container. The device includes a receiver coil for receiving alternating current power via electromagnetic induction. The electromagnetic induction occurs across a wall of the nuclear material storage container. The device includes a rectifier for rectifying the alternating current power into direct current power. The device includes one or more sensors for creating the data describing the one or more conditions existing within the nuclear material storage container. The device includes one or more data transmitters for transmitting the data to one or more data receivers located external to the nuclear material storage container.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

DETAILED DESCRIPTION OF THE INVENTION

Figure 1:
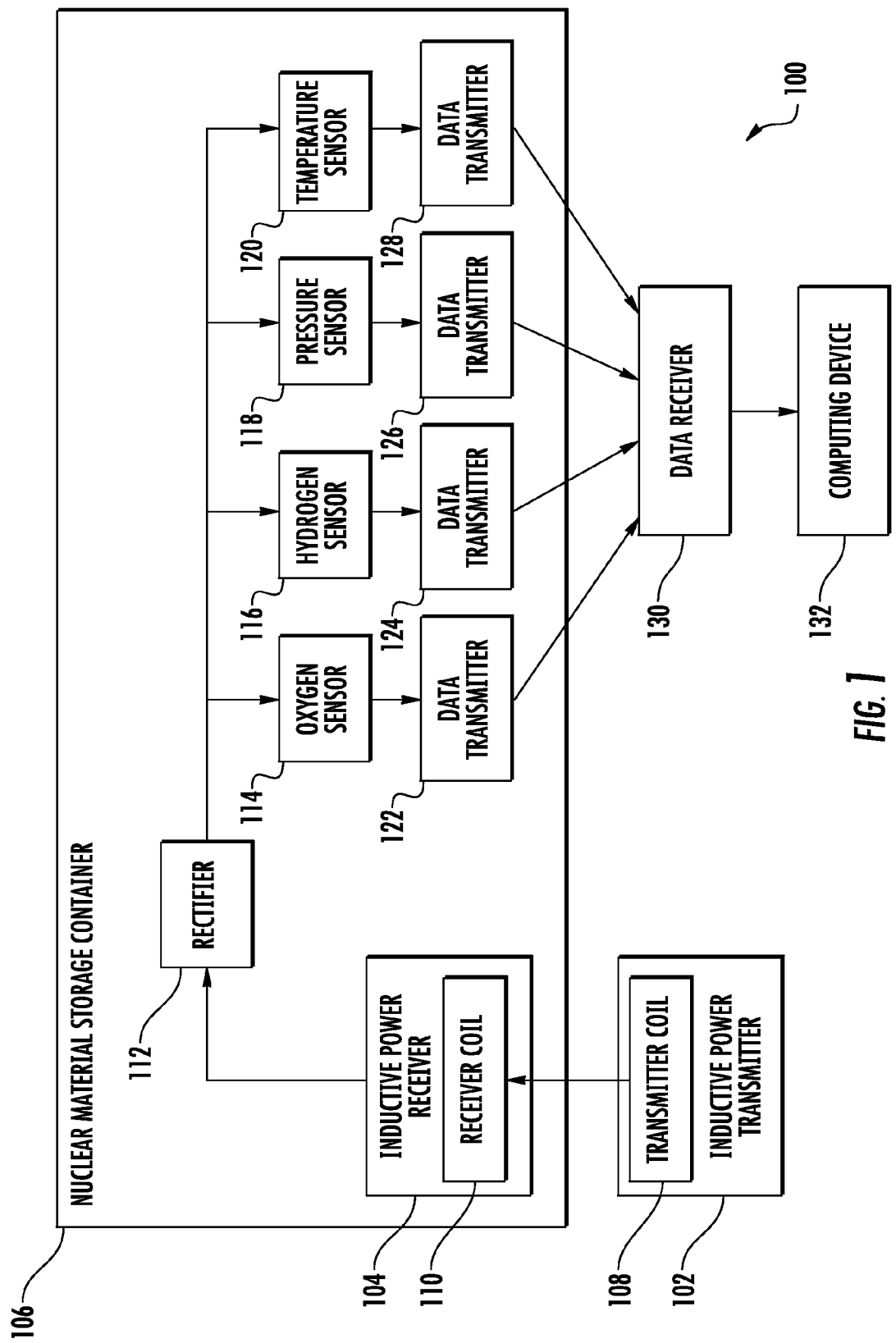
FIG. 1 depicts an example passive gas monitoring system according to an example embodiment of the present disclosure.

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

Generally, the present disclosure is directed to gas monitoring systems that use inductive power transfer to safely power an electrically passive device included within a nuclear material storage container. In particular, the electrically passive device can include an inductive power receiver for receiving inductive power transfer through a wall of the nuclear material storage container. The power received by the inductive power receiver can be used to power one or more sensors included in the device. Thus, the device is not required to include active power generation components such as, for example, a battery, thereby decreasing the risk of a spark igniting flammable gases within the container. In addition, use of inductive power transfer allows for power to be provided on-demand at any point throughout the duration of a storage period, thereby eliminating concerns regarding battery life.

As an example, the inductive power receiver can include a receiver coil and a capacitor. The receiver coil can be inductively coupled to a transmitter coil included in an inductive power transmitter that is external to the storage container.

The inductive power transmitter can include an alternating current source that creates an alternating current across the transmitter coil, thereby creating a magnetic field. For example, in some implementations, the inductive power transmitter can operate to generate a magnetic field that oscillates at about 131 kilohertz.

When the transmitter coil and the receiver coil are positioned appropriately with respect to one another, the magnetic field generated by the transmitter coil can induce alternating current flow across the receiver coil. The alternating current across the receiver coil can be used to charge the capacitor.

The device can also include a rectifier for converting the received alternating current power into direct current power. The direct current power can be used to power the one or more sensors for monitoring conditions within the nuclear material storage container. For example, the direct current power output by the rectifier can be used as a direct current voltage bus for the electrically passive device.

The one or more sensors included within the nuclear material storage container can include a hydrogen concentration sensor, an oxygen concentration sensor, a pressure sensor, and/or a temperature sensor. As an example, in some implementations, the sensors can be positioned within a containment vessel included in the nuclear material storage container. Further, in some implementations, the entirety of the electrically passive device is located within the containment vessel.

In particular, the containment vessel can contain nuclear waste or other radioactive materials. Thus, positioning the sensors within the containment vessel can allow the device to monitor the conditions associated with the radioactive materials more precisely. In other implementations, the sensors may be located at various other locations that are also in gaseous communication with the radioactive material.

The device can also include one or more data transmitters for transmitting the data output by the one or more sensors to a data receiver located external to the nuclear material storage container. As an example, in some implementations, each sensor is associated with its own respective data transmission components.

Each of the one or more data transmitters can include a micro controller and a micro modem. For example, the micro modems can be Rubee® IEEE 1902.1 micro modems. The data transmitters can be powered by the direct current voltage bus as well.

In such fashion, an electrically passive device can provide data describing existing conditions within a sealed nuclear material storage container. In particular, the passive device can be powered using only inductive power transfer. Therefore, the device is wholly passive in nature and does not present a risk of a spark igniting any flammable gases potentially present within the container. In addition, use of inductive power transfer provides the ability to power the device on-demand and at any point during the lifespan of the storage container, regardless of the length of storage period.

With reference now to the FIGS., example embodiments of the present disclosure will be discussed in further detail. FIG. 1 depicts example passive gas monitoring system 100 according to an example embodiment of the present disclosure. System 100 can include an inductive power transmitter 102 providing power to an inductive power receiver 104 through the wall of a nuclear material storage container 106.

Figure 2:
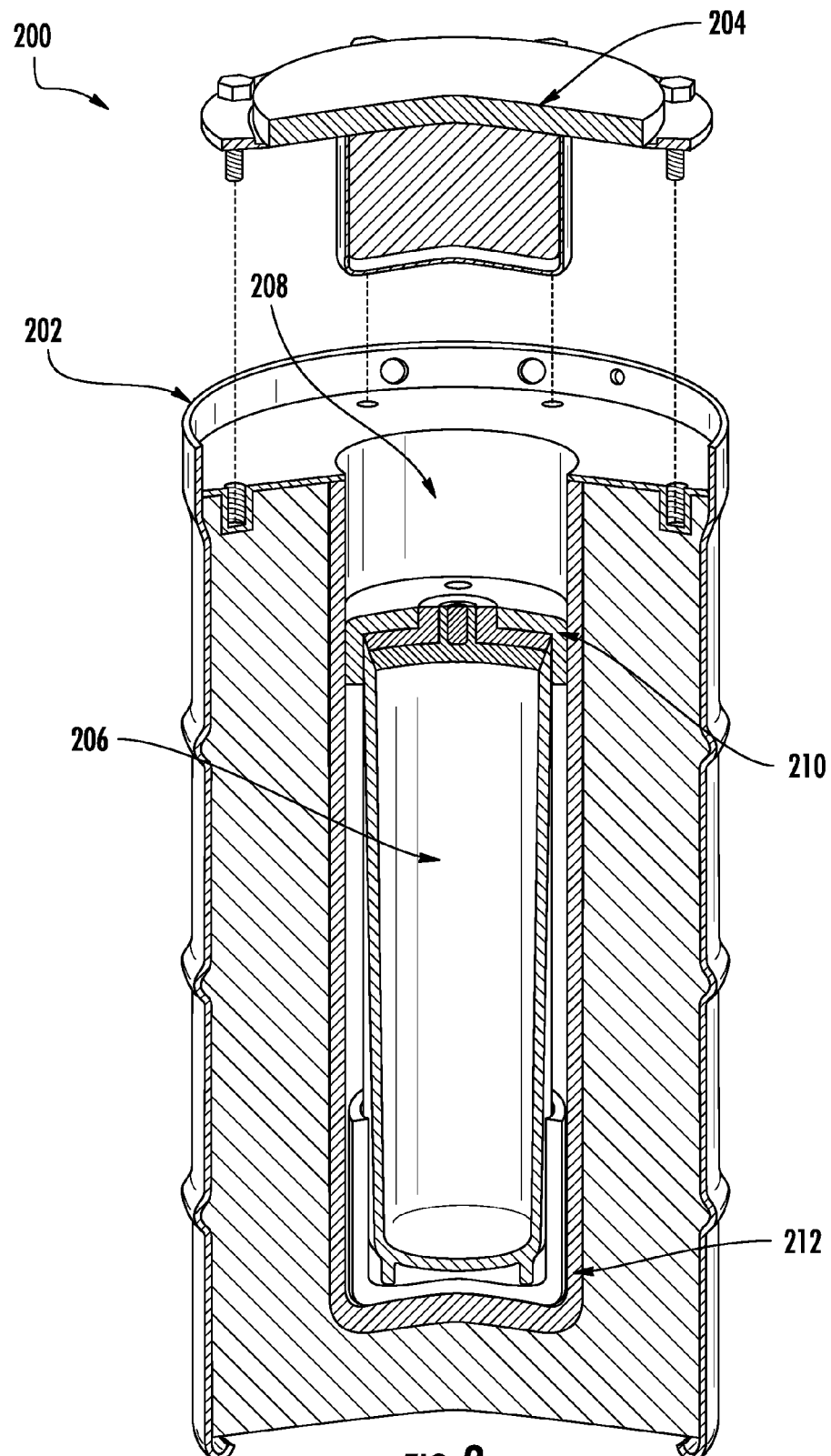
FIG. 2 depicts an example nuclear material storage container according to an example embodiment of the present disclosure.

As an example, FIG. 2 depicts an example nuclear material storage container 200 according to an example embodiment of the present disclosure. Storage container 200 can include a drum 202 and a lid 204.

A containment vessel or shell 206 can be disposed within a cavity 208. The containment vessel 206 can hold nuclear waste or other radioactive material. In some implementations of the present disclosure, an electrically passive device containing one or more sensors can be positioned within containment vessel 206.

Containment vessel 206 can be supported by a bottom load distribution fixture 212 and a top load distribution fixture 210. It will be appreciated that nuclear material storage container 200 includes many other sophisticated features and materials for increasing safety that are not expressly discussed herein.

Referring again to FIG. 1, the inductive power transmitter 102 can provide power to the inductive power receiver 104 using electromagnetic induction. As an example, a transmitter coil 108 can be included within inductive power transmitter 102. Likewise, a receiver coil 110 can be included within inductive power receiver 104.

Transmitter coil 108 and receiver 110 can be inductively coupled such that current flow through transmitter coil 108 induces the flow of current through receiver coil 110. More particularly, transmitter coil 108 and receiver coil 110 can be positioned relative to one another such that a magnetic field created by a first current flowing through transmitter coil 108 induces a second current to flow through receiver coil 110.

Transmitter coil 108 and receiver coil 110 can each have any suitable diameter and are not required to be identically sized with respect to each other.

In addition, although FIG. 1 depicts a transmitter coil 108 and a receiver coil 110, it will be appreciated that, in alternative implementations, inductive power transmitter 102 and inductive po wer receiver 104 can perform inductive power transfer using various inductive components that are not coil-shaped.

Figure 3:
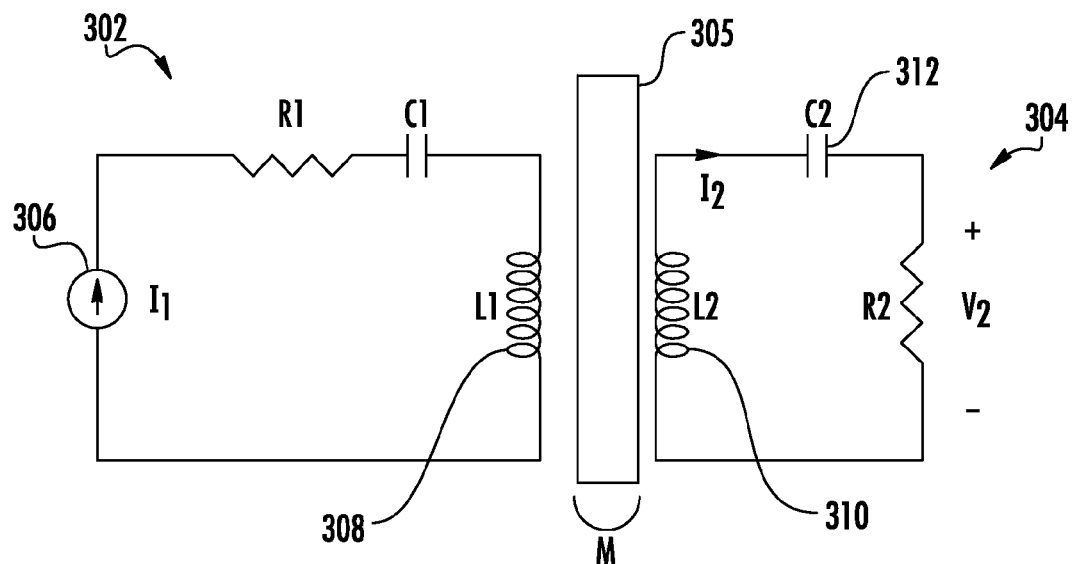
FIG. 3 depicts an example inductive power transmitter and an example inductive power receiver according to an example embodiment of the present disclosure.

As an example, FIG. 3 depicts an example inductive power transmitter 302 and an example inductive power receiver 304 according to an example embodiment of the present disclosure.

Inductive power transmitter 302 is capable of providing power to inductive power receiver 304 through a wall 305 of a nuclear material storage container using electromagnetic induction. For example, wall 305 can include varying materials such as a stainless steel drum wall, polyurethane foam, other forms of insulation, and/or a stainless steel containment vessel wall.

Inductive power transmitter 302 can include an alternating current source 306 and a first inductive element 308. Alternating current source 306 can generate alternating current having a generally consistent amplitude and/or frequency. For example, in some implementations, alternating current source 306 can generate an alternating current having a frequency at about 131 kilohertz.

First inductive element 308 can be any component that, upon the application of a current, generates a magnetic field suitable for performing inductive power transfer. For example, first inductive element 308 can be a transmission coil.

Inductive power receiver 304 can include a second inductive element 310 and a capacitor 312. Second inductive element can be any component that, upon the application of a magnetic field, generates a current. For example, second inductive element 310 can be a receiver coil.

Current generated by the application of the magnetic field to second inductive element 310 can be used to charge a capacitor 312. In particular, a voltage ($V_2$) can be generated, for example, across a resistor as shown in FIG. 3.

The output voltage ($V_2$) of inductive power receiver 304 can be dependent upon the current ($I_2$) generated in the loop of inductive power receiver 304. For example, the output voltage can be expressed as $V_2=j\omega M(I_2)$, where M is based on material properties of wall 305, where $\omega=2\pi f$, and where f is the frequency of the current generated by alternating current source 306. Furthermore, the various values of the capacitive and resistive components depicted in FIG. 3 can be modified to tune the magnetic field wave.

In particular, as an example, use of alternating current having a frequency of about 131 kilohertz has been shown to be capable of transferring power through a drum wall, insulative material, and a wall of a containment vessel, such as, for example, shown in FIG. 2.

Referring again to FIG. 1, a rectifier 112 can also be included within nuclear material storage container 106. Rectifier 112 can be coupled to inductive power receiver 104. Rectifier 112 can receive alternating current power from inductive power receiver 104 and convert or otherwise condition the alternating current power into direct current power.

Rectifier 112 can provide the direct current power as an output. As an example, in some implementations, the direct current power output by rectifier 112 can be used as a direct current voltage bus for a number of different components included within nuclear material storage container 106.

Figure 4:
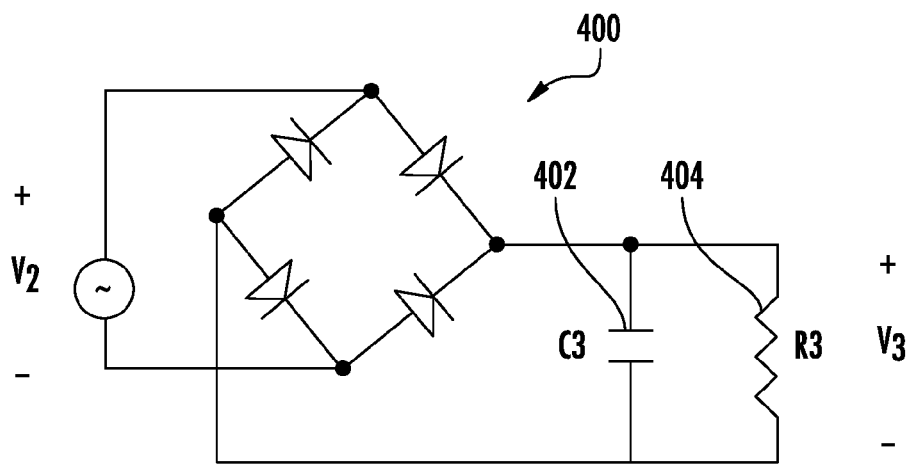
FIG. 4 depicts an example rectifier according to an example embodiment of the present disclosure.

As an example, FIG. 4 depicts an example rectifier 400 according to an example embodiment of the present disclosure. Rectifier 400 can convert an alternating current voltage ($V_2$) into a direct current voltage ($V_3$), as is generally known in the art.

In particular, rectifier 400 is a full bridge rectifier. However, other forms of rectifiers or converters can be used as well, such as, for example, half bridge rectifiers or other voltage converters.

Rectifier 400 can include a capacitor 402 and a resistor 404. The values of capacitor 402 and resistor 404 can be varied to provide a variable time constant of the rectifier 400 output circuit. The time constant will determine the voltage decay of the rectifier 400 output circuit after the inductive power transmitter ceases to provide inductive power.

Figure 5:
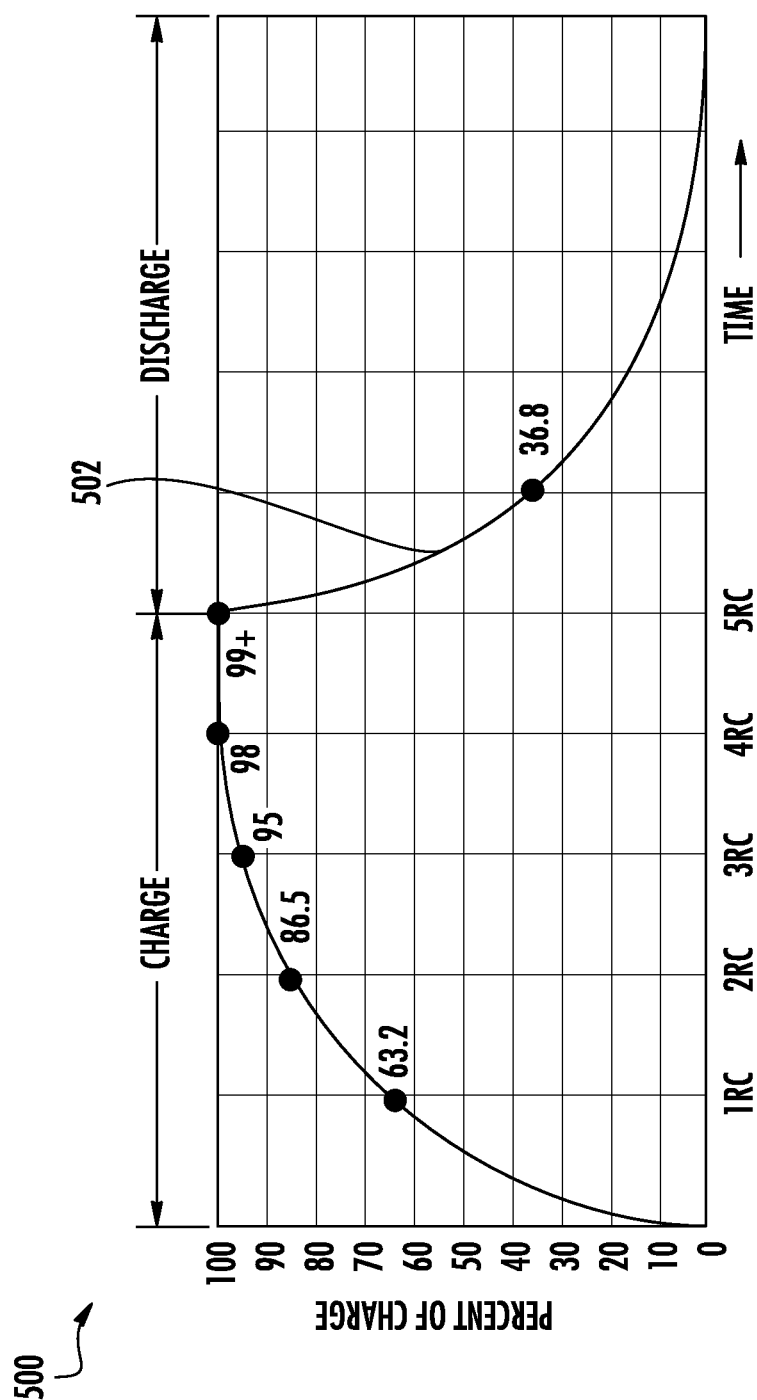
FIG. 5 provides a graphical depiction of an example charge discharge curve according to an example embodiment of the present disclosure.

As an example, FIG. 5 provides a graphical depiction 500 of an example charge discharge curve 502 according to an example embodiment of the present disclosure. As shown by graphical depiction 500, varying the value of RC will result in increasing or decreasing the charge and discharge periods. Thus, the value of RC can be chosen based on a desired length of time that the electrically passive circuit included in the nuclear material containment vessel should remain charged following disapplication of inductive power. In particular, the circuits of the present disclosure can all be designed to fully decay prior to transport or long term storage of the container.

Referring again to FIG. 1, one or more sensors can be coupled to the output of rectifier 112 and can monitor conditions within nuclear material storage container 106. For example, the one or more sensors can include an oxygen concentration sensor 114, a hydrogen concentration sensor 116, a pressure sensor 118, and a temperature sensor 120.

As will be discussed further below, each of sensors 114-120 can be coupled to a data transmitter. Furthermore, all electrical connections associated with each of sensors 114-120 and other components of the passive device can be sealed in epoxy so as to reduce the risk of an electrical spark igniting flammable gases.

Sensors 114-120 can monitor conditions inside nuclear material storage container 106. As an example, in some implementations, sensors 114-120 can be in gaseous communication with a radioactive material stored in nuclear material storage container 106. For example, in some implementations, sensors 114-120 can be positioned within a containment vessel of nuclear material storage container 106.

Figure 6:
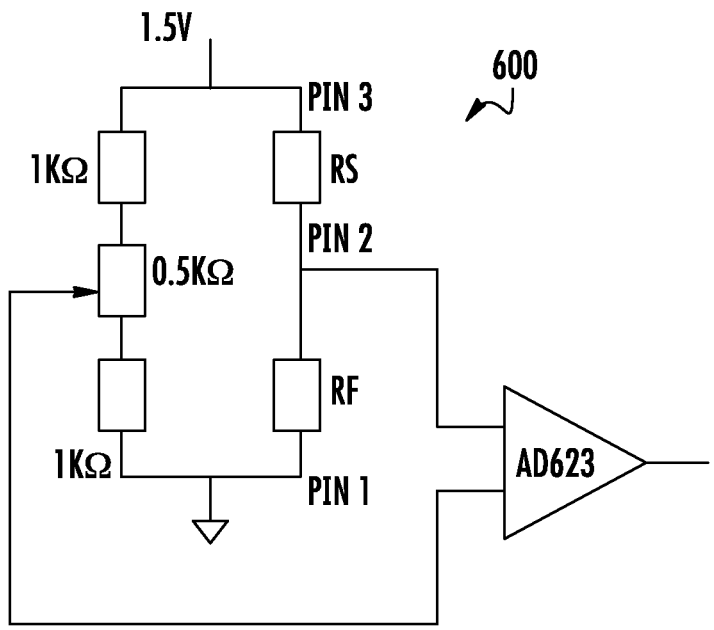
FIG. 6 depicts an example hydrogen concentration sensor circuit according to an example embodiment of the present disclosure.

As an example, FIG. 6 depicts an example hydrogen concentration sensor circuit 600 according to an example embodiment of the present disclosure. Circuit 600 can include a Kebaili® KHS-200 MEMS micro-pellistor packaged in a three pin TO-18 package.

This sensor is compact and low power, with a maximum power draw of thirty milliwatts and a one second response time. The 1.5 volts input can be received from rectifier 400 from FIG. 4 or a different rectifier or voltage source.

The sensor has two internal resistances. A first resistance (RS) can be used for sensing the change in hydrogen concentration. A second resistance (RF) can be used as a reference cell for compensating for resistance changes not due to hydrogen concentration changes.

The output voltage from the Analog Devices® AD623 shown in FIG. 6 can be coupled to a data transmitter for transmission of data to a receiver external to the container.

In addition, a circuit similar to circuit 600 of FIG. 6 can be used as a resistance temperature detector. In particular, the second resistance (RF) can again be used as a fixed resistor while the first resistance (RS) can change resistance in response to changes in temperature.

Figure 7:
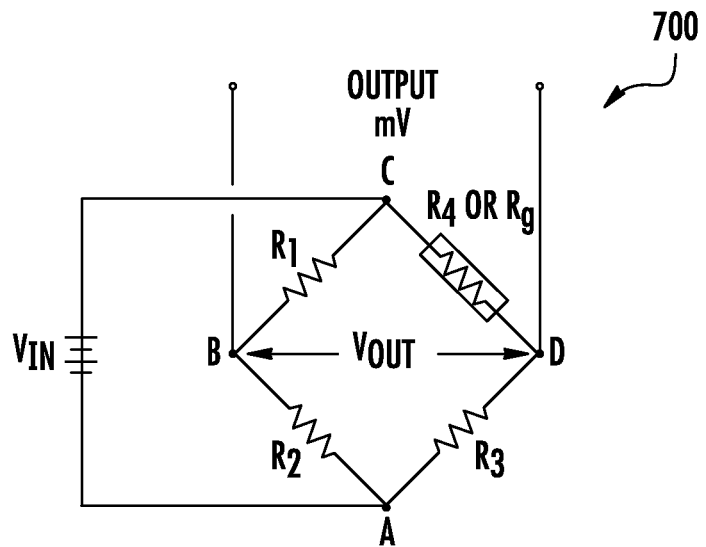
FIG. 7 depicts an example pressure sensor circuit according to an example embodiment of the present disclosure.

As another example, FIG. 7 depicts an example pressure sensor circuit 700 according to an example embodiment of the present disclosure. In particular, circuit 700 can include an Endevco® 8410B piezo resistance strain gage with a range of zero to one psig. This sensor has the sensitivity to detect a very small amount of gas generated in a sealed container, such as a nuclear material storage or shipping container. Circuit 700 shows an active arm R4, which can be the Endevco® 8410B or other similar sensor.

In addition, the input voltage ($V_{IN}$) can be received from rectifier 400 from FIG. 4 or a different rectifier or voltage source. The output voltage ($V_{OUT}$) can be coupled to a data transmitter for transmission of data to a receiver external to the container.

Figure 8:
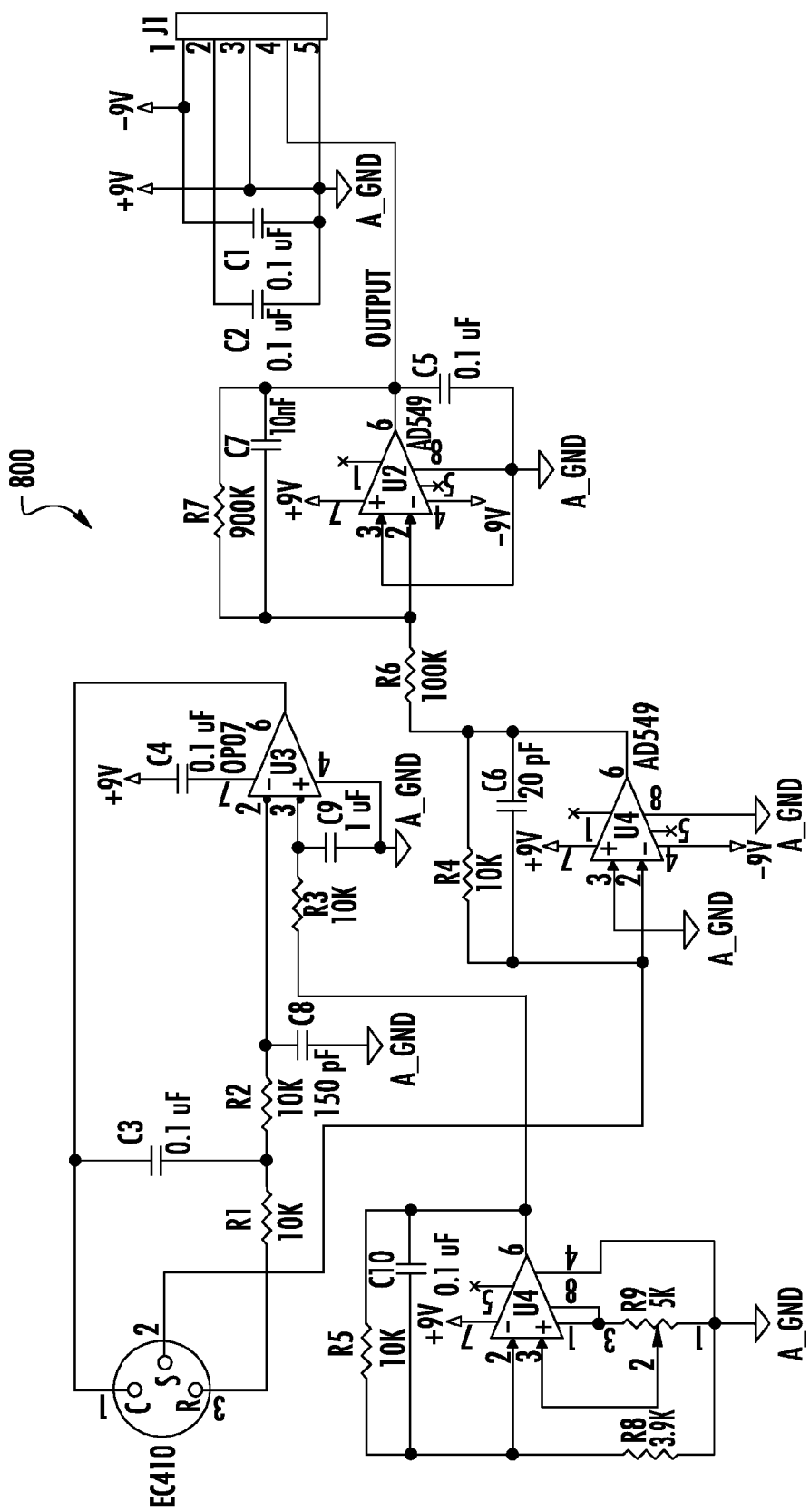
FIG. 8 depicts an example oxygen concentration sensor circuit according to an example embodiment of the present disclosure.

As another example, FIG. 8 depicts an example oxygen concentration sensor circuit 800 according to an example embodiment of the present disclosure. Circuit 800 can include a sealed electrochemical oxygen sensor, such as, for example, the e2V Technologies® EC410 Oxygen Sensor.

Referring again to FIG. 1, as mentioned above, sensors 114-120 can be respectively coupled to data transmitters 122, 124, 126, and 128. Although not explicitly shown in FIG. 1, each of data transmitters 122-128 can receive power from rectifier 112.

Each of data transmitters 122-128 can include a micro controller and a micro modem. For example, the micro controller can be an Epson® S1c60 micro controller with an analog input. The micro controller can connected via a serial link to a Rubee® IEEE 1902.1 micro modem.

The Rubee® micro modem has been shown to transmit bi-directionally from the inside of a containment vessel included in a nuclear material storage container 106 to a data receiver 130 located exterior to the storage container 106. In particular, bi-directional data transmission can occur using a 131 kilohertz magnetic field wave.

In addition, although data transmitters 122-128 are respectively provided for sensors 114-120 in FIG. 1, in some implementations, a single data transmitter can provide data transmission functionality for all of the sensors.

Data receiver 130 can be any device for receiving data transmitted from data transmitters 122-128. For example, data receiver 130 can be a pickup antenna for receiving magnetic field waves. Data receiver 130 can provide received signals to a computing device 132 for analysis and processing.

Figure 9:
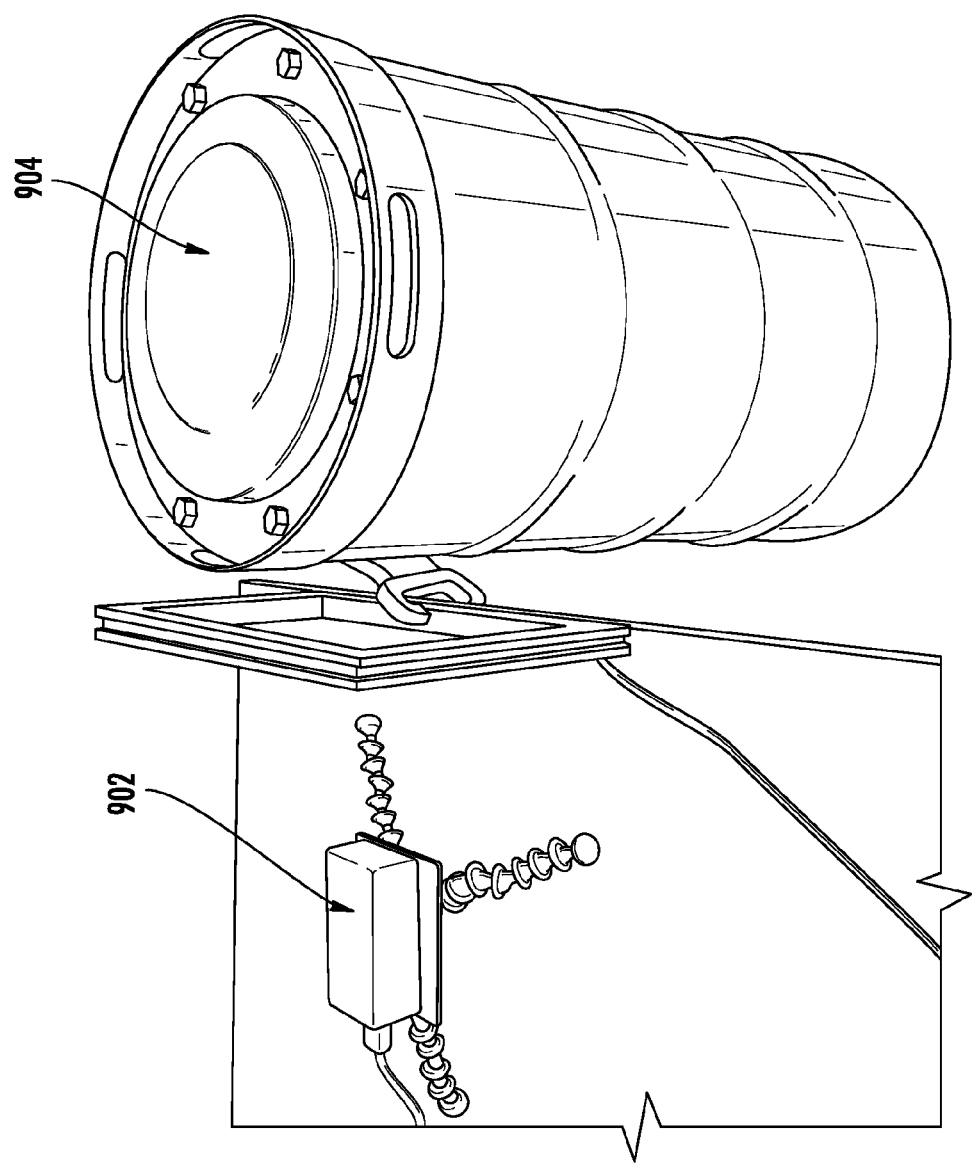
FIG. 9 depicts an example data receiver and example nuclear material storage container according to an example embodiment of the present disclosure.

As an example, FIG. 9 depicts an example data receiver 902 and example nuclear material storage container 904 according to an example embodiment of the present disclosure.

More particularly, one or more sensors can be included within storage container 904. The one or more sensors can be powered through inductive power transfer and provide data describing internal gaseous conditions to a data transmitter. The data transmitter can transmit the data to the data receiver 902.

In such fashion, internal conditions of storage container 904 can be monitored prior to shipment or long term storage without introducing a power generation component into storage container 904 and also without unsealing storage container 904, as shown in FIG. 9.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A passive gas monitoring system, the system comprising:
    an inductive power receiver positioned within a nuclear material storage container, wherein the inductive power receiver is configured to receive power from an inductive power transmitter positioned outside the nuclear material storage container using inductive power transfer;
    one or more sensors positioned within the nuclear material storage container, wherein the one or more sensors are configured to respectively provide one or more outputs respectively describing one or more conditions within the nuclear material storage container, wherein the one or more sensors receive power from the inductive power receiver, and wherein the one or more sensors comprise:
        a first sensor for measuring hydrogen concentration; and
        a second sensor for measuring oxygen concentration; and
    at least one data transmitter positioned within the nuclear material storage container, wherein the at least one data transmitter is configured to transmit the one or more outputs respectively provided by the one or more sensors to a data receiver positioned outside the nuclear material storage container.

2. The passive gas monitoring system of claim 1, wherein the power received by the inductive power receiver comprises the sole source of power used to power the one or more sensors and the at least one data transmitter such that all system components positioned within the nuclear material storage container are passive in nature.

3. The passive gas monitoring system of claim 1, wherein:
    the inductive power receiver comprises a receiver coil and a capacitor; and
    current flow through the receiver coil charges the capacitor.

4. The passive gas monitoring system of claim 1, further comprising the inductive power transmitter.

5. The passive gas monitoring system of claim 4, wherein the inductive power transmitter comprises a transmitter coil.

6. The passive gas monitoring system of claim 4, wherein the inductive power transmitter further comprises a current source providing alternating current.

7. The passive gas monitoring system of claim 6, wherein the alternating current comprises alternating current having a frequency at about 131 kilohertz.

8. The passive gas monitoring system of claim 1, wherein the one or more sensors are positioned within a containment vessel included in the nuclear material storage container.

9. The passive gas monitoring system of claim 1, wherein the first sensor and the second sensor are positioned so as to be in gaseous communication with a material stored by the nuclear material storage container.

10. The passive gas monitoring system of claim 1, wherein the one or more sensors further comprise:
   a third sensor for measuring temperature; and
   a fourth sensor for measuring pressure.

11. A device for measuring gas characteristics within a radioactive material container, the device comprising:
   an inductive power receiver for receiving inductive power transfer through a wall of the radioactive material container;
   a rectifier coupled to the inductive power receiver, wherein an output of the rectifier comprises a direct current voltage bus of the device;
   at least one of an oxygen concentration sensor or a hydrogen concentration sensor coupled to the output of the rectifier; and
   at least one data transmission component for receiving data from the at least one of the oxygen concentration sensor and the hydrogen concentration sensor and transmitting the data to a data receiver that is external to the radioactive material container;
   wherein the device does not contain any power generation components such that the device is wholly passive in nature.

12. The device of claim 11, wherein:
   a radioactive material is stored within a containment vessel included in the radioactive material container; and
   the device is positioned within the containment vessel.

13. The device of claim 11, wherein the inductive power transfer occurs using a magnetic field that oscillates at about 131 kilohertz.

14. A passive gas monitoring system, the system comprising:
   an inductive power receiver positioned within a nuclear material storage container, wherein the inductive power receiver is configured to receive power from an inductive power transmitter positioned outside the nuclear material storage container using inductive power transfer;
   one or more sensors positioned within the nuclear material storage container, wherein the one or more sensors are configured to respectively provide one or more outputs respectively describing one or more conditions within the nuclear material storage container, and wherein the one or more sensors receive power from the inductive power receiver; and
   at least one data transmitter positioned within the nuclear material storage containe wherein the at least one data transmitter is configured to transmit the one or more outputs respectively provided b r the one or more sensors to a data receiver positioned outside the nuclear material storage container;
   wherein the one or more sensors comprise a plurality of sensors; and
   wherein the at least one data transmitter comprises a plurality of data transmitters respectively associated with the plurality of sensors.

15. The passive gas monitoring system of claim 14, wherein the power received by the inductive power receiver comprises the sole source of power used to power the plurality of sensors and the plurality of data transmitters such that all system components positioned within the nuclear material storage container are passive in nature.

16. The passive gas monitoring system of claim 14, wherein the plurality of sensors comprise:
   a first sensor for measuring hydrogen concentration; and
   a second sensor for measuring oxygen concentration.

17. The passive gas monitoring system of claim 14, wherein the one or more sensors comprise:
   a first sensor for measuring hydrogen concentration; and
   a second sensor for measuring oxygen concentration.

18. A passive gas monitoring system, the system comprising:
   an inductive power receiver positioned within a nuclear material storage container, wherein the inductive power receiver is configured to receive power from an inductive power transmitter positioned outside the nuclear material storage container using inductive power transfer;
   one or more sensors positioned within the nuclear material storage container, wherein the one or more sensors are configured to respectively provide one or more outputs respectively describing one or more conditions within the nuclear material storage container, and wherein the one or more sensors receive power from the inductive power receiver; and
   at least one data transmitter positioned within the nuclear material storage container, wherein the at least one data transmitter is configured to transmit the one or more outputs respectively provided by the one or more sensors to a data receiver positioned outside the nuclear material storage container;
   wherein one or more electrical connections associated with the one or more sensors are sealed in an epoxy so as to decrease a risk of a spark event.

19. The passive gas monitoring system of claim 18, wherein the power received by the inductive power receiver comprises the sole source of power used to power the one or more sensors and the at least one data transmitter such that all system components positioned within the nuclear material storage container are passive in nature.

* * * * *